Figure 1:
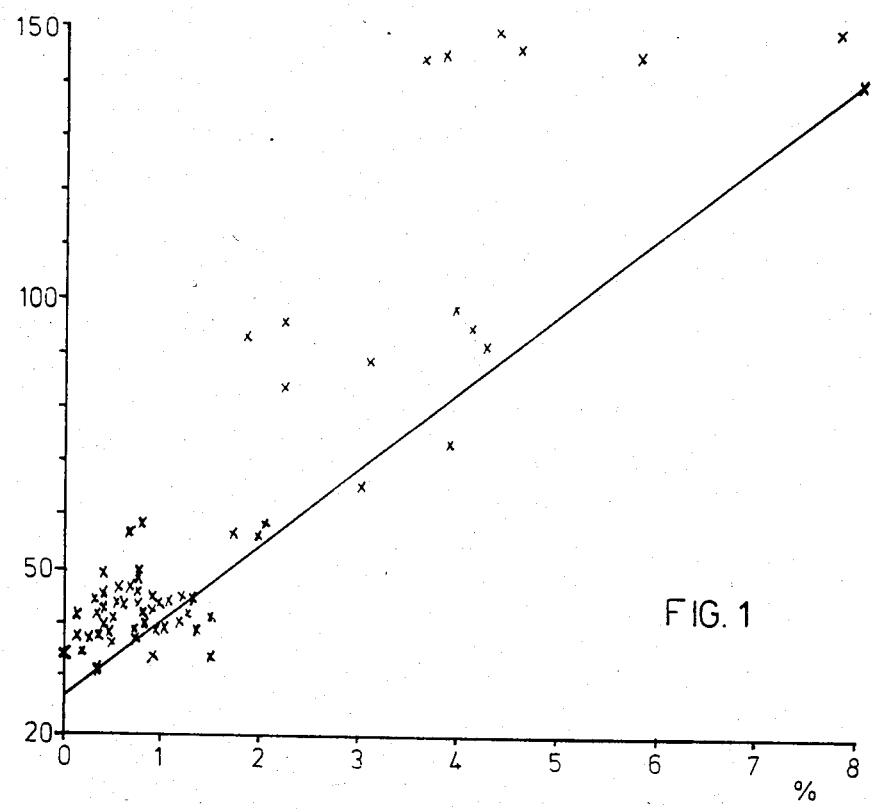

United States Patent [19]

Arend et al.

[11] Patent Number: 4,528,388
[45] Date of Patent: Jul. 9, 1985

[54] XANTHOGEN DISULPHIDES

[75] Inventors: Günter Arend, Dormagen; Heinrich Königshofen, Bergisch-Gladbach; Peter Müller, Kerpen; Rüdiger Musch, Bergisch-Gladbach, all of Fed. Rep. of Germany

[73] Assignee: Bayer Aktiengesellschaft, Leverkusen, Fed. Rep. of Germany

[21] Appl. No.: 323,993

[22] Filed: Nov. 23, 1981

[30] Foreign Application Priority Data

Nov. 28, 1980 [DE] Fed. Rep. of Germany ....... 3044811

[51] Int. Cl.$^3$ ............................................ C07D 317/12
[52] U.S. Cl. ................................................... 549/448
[58] Field of Search .................... 260/455 B; 549/448

[56] References Cited

U.S. PATENT DOCUMENTS 2,904,554 9/1959 Wheeler et al. ..................... 548/463
3,067,211 12/1962 Inman et al. .......................... 549/63

Primary Examiner—Henry R. Jiles
Assistant Examiner—Robert C. Whittenbaugh
Attorney, Agent, or Firm—Connolly and Hutz

[57] ABSTRACT

Xanthogen disulphides of the following formula:

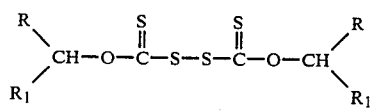

wherein
R and $R_1$ independently represent hydrogen, $C_1$–$C_6$ alkyl, $C_5$–$C_8$-cycloalkyl or an oxygen-containing heterocyclic ring system having from 5 to 8 ring members and optionally mono- or tri-substituted by $C_1$–$C_4$-alkyl, and wherein
R and $R_1$ may also be connected together to complete a hetero cyclic ring having from 3 to 6 carbon atoms and from 1 to 3 oxygen ring members, and the ring may be substituted by from 1 to 3 $C_1$–$C_4$-alkyl groups, with a content of elemental sulphur of less than 1.7% by weight, a process for their production by the reaction of a xanthic acid-O-ester-alkali metal salt of the following formula:

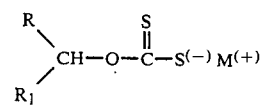

wherein
R and $R_1$ are as defined in claims 1 and 3, and
M represents an alkali metal, with aqueous chlorine bleach liquor, characterized in that aqueous chlorine bleach liquor having a concentration of less than 0.9 mol NaOCl/kg is used, and oxidation is carried out at a temperature of from 10° to 20° C. and at a pH of from 8 to 12, only until from 0.1 to 5.0 mol % of the xanthic acid-O-ester-alkali metal salt, based on the quantity used, is still present at the end of the reaction, as well as their use as molecular weight regulators in the polymerization of chloroprene.

2 Claims, 2 Drawing Figures

XANTHOGEN DISULPHIDES

This invention relates to xanthogen disulphides having a content of elemental sulphur of less than 1.7% by weight, a process for the production thereof by the oxidation of xanthic acid-O-ester-alkali metal salts with chlorine bleach liquor, and the use thereof as molecular weight regulators in the polymerisation of chloroprene to form light coloured polymers.

Xanthogen disulphides are important molecular weight regulators in the polymerisation of unsaturated monomers, in particular chloroprene. It must be possible to obtain the products in a high yield and with a good purity. Processes for the production of xanthogen disulphides are frequently described in the literature. By reacting alcohols with carbon disulphide in the presence of at least equimolar quantities of alkali, xanthic acid-O-ester salts are produced which may be oxidised to form xanthogen disulphides. Iodine or copper sulphate were originally used as oxidizing agents (Zeise: Schw. J. 1822, 36; Berz. J. 1824, 3, 82; 1837, 16, 306; Ann. Phys. 1835, 35, 489 and "Houben-Weyl, Meth. der Organ. Chemie"; volume 9, P. 812 (1955)), and subsequently the following were mentioned as oxidizing agents: sodium tetrathionate, cyanogen bromide, nitrous acid, chloramine-T, nitrosylchloride (see Cambron, Whitby: Canadian J. Res., 1930, 2, 144) and an electrolytic process was also described (Schall: Z. Elektrochem. 1895, 2, 475). Potassium peroxodisulphate or hydrogen peroxide are also mentioned as oxidizing agents in German Offenlegungsschrift No. 2,306,610. However, these oxidizing agents are too expensive for large-scale use and they cannot be used readily for reasons of safety. Chlorine vapour or bromine vapour, optionally diluted with air, are proposed as oxidizing agents in U.S. Pat. No. 2,375,083 and in German Offenlegungsschrift No. 2,533,989.

All these processes usually produce good yields.

However, unless a purification step is included, the resulting purities are inadequate for the practical use of these disulphides as polymerisation regulators, although the compounds appear pure by elemental analysis. Therefore, it is proposed in Canadian Pat. No. 856,834 to carry out the oxidation process of the xanthates with chlorine bleach liquor in an aqueous system in the presence of a lower aliphatic alcohol, in particular isopropanol. As a result of simultaneously using alcohol, products are obtained which are light in colour and which have a small melting point interval.

The xanthogen disulphides produced in a purely aqueous system by chlorine, chlorine bleach liquor, chloramine-T or persulphate oxidation may be obtained in such a pure yield, optionally by repeated distillation or re-crystallisation, that they may be used as molecular weight regulators. However, it is only possible to carry out these purification operations commercially at considerable expense. Thus, it is possible to distill diethyl xanthogen disulphide at a pressure of 0.05 mm, but the compound decomposes quantitatively at 18 mm during the attempted distillation operation (Tschugaaeff-Reaction, in this regard, see Bulmer, Mann: j. Chem. Soc. 1945, 674 ff.). Many xanthogen disulphides may be re-crystallised, but only small temperature differences for re-crystallisation may be used, owing to the great instability of the xanthogen disulphides under thermal stress. Thus, this purification method is also problematic and it results in excessive losses in yield. A regeneration of the solvents used is also necessary, which is likewise only possible commercially if particular precautions are taken, in view of the great thermal instability of the dissolved xanthate residues (Tschugaeff Reaction: mercaptan formation!). A process allowing the production of xanthogen disulphides in a very pure form and using cheap oxidizing agents in an aqueous medium would therefore constitute significant technical progress.

In order to determine the purity of the xanthogen disulphides, in addition to the conventional physical data, their suitability as molecular weight regulators in chloroprene polymerisation was also tested. During this test, chloroprene was polymerised in a standard mixture with the addition of fixed quantities of xanthogen disulphide, the resulting elastomer was processed and the Mooney viscosity was determined (see Example 1a).

In the case of bis-(5-ethyl-1,3-dioxan-5-yl)-methyl xanthogen disulphide (abbreviated to "MTX"), good product qualities produce a Mooney viscosity (ML-4' value) of at most 50, on average from 35 to 45; in poor batches, ML-4' was to some extent found to be >100. A correlation between the Mooney viscosity of the elastomer in the standard mixture and the sulphur content in the MTX found by HPLC analysis (see Example 1b with respect to the HPLC analysis of the MTX) could be established by examining all the specification values of the regulator. Owing to the low absolute sulphur content in the xanthogen disulphide, the analysis is naturally subject to a relatively large error, so that the correlation was corroborated statistically. On graph number 1 is plotted the dependence of the ML-4' value on the sulphur content and each point corresponds to the result of a polymerisation experiment of chloroprene using respectively varying experimental batches of MTX. It may be seen that the specification upper limit of ML-4'=50 is regularly exceeded when the sulphur content in the regulator amounts to more than from 1.5 to 1.7%. Therefore, the defective regulator effect which is observed and which was mentioned in the patent literature (for example, Canadian Pat. No. 856,834) of xanthogen disulphides produced in a purely aqueous medium is attributed to a content of elemental sulphur.

This sulphur content cannot be detected by a distortion of the elemental analysis results or by a melting point depression.

The higher sulphur content of poorer regulator batches may also be correlated with the consumption of activator solution during the polymerisation process of chloroprene (see Example 1 and Table 1). Polymers which were produced using MTX with a high sulphur content show a considerable increase in the Mooney value during hot air storage (3 days at 70° C.).

Therefore, the present invention provides xanthogen disulphides of the following formula:

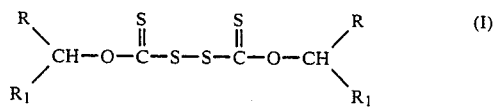

wherein

R and $R_1$ independently represent hydrogen, $C_1$–$C_6$-alkyl, $C_5$–$C_8$-cycloalkyl or an oxygen-containing heterocyclic ring system having from 5 to 8 ring members and optionally mono- to tri-substituted by $C_1$–$C_4$-alkyl, and wherein R and $R_1$ may also be connected together to complete a heterocyclic ring having from 3 to 6 carbon atoms and from 1 to 3 oxygen ring members, the ring optionally being substituted by from 1 to 3 $C_1$-$C_4$-alkyl groups, having a content of elemental sulphur of less than 1.7% by weight, preferably less than 1.2% by weight.

The following are mentioned by way of example as xanthogen disulphides of the above formula: dimethyl xanthogen disulphide, diethyl xanthogen disulphide, dipropyl xanthogen disulphide, dibutyl xanthogen disulphide, dicyclohexyl xanthogen disulphide, bis(1,3-dioxolan-4-yl-methyl)xanthogen disulphide, bis-(5-ethyl-1,3-dioxan-5-yl-methyl)xanthogen disulphide (MTX) and diisopropyl xanthogen disulphide.

R preferably represents hydrogen and $R_1$ preferably represents 5-ethyl-1,3-dioxan-5-yl or 1,3-dioxolan-4-yl.

The present invention also provides a process for the production of xanthogen disulphides by the reaction of a xanthic acid-O-ester-alkali metal salt of the following formula:

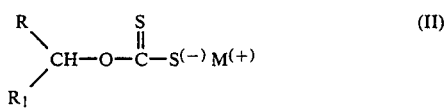

(II)

wherein

R and $R_1$ are as defined above, and

M represents an alkali metal, preferably sodium or potassium, with aqueous chlorine bleach liquor, characterised in that aqueous chlorine bleach liquor having a concentration of less than 0.9 mol NaOCl/kg, preferably from 0.4 to 0.7 mol/kg, is used and oxidation is carried out at a temperature of from 10° to 20° C., preferably from 0° to 10° C., and at a pH of from 8 to 12, preferably from 8 to 11, only until the xanthic acid-O-ester-alkali metal salt is still present in an amount of from 0.1 to 5 mol %, preferably to from 1 to 3 mol %, based on the quantity used, at the end of the reaction.

The end point of the reaction according to the invention may be easily determined iodometrically. According to known processes, the xanthogen disulphide which has formed is isolated, such as, for example, by being separated as the liquid phase or optionally filtered off as solid substance and dried.

The oxidation process is sensitive to deviations from the reaction conditions mentioned, in particular to the use of higher-concentrated chlorine bleach liquor, to working at too high a temperature or at too low a pH, and to over-oxidation which may also easily occur locally as a result of inadequate blending. In the case of large-scale mixtures, the effect of such deviations is that xanthogen disulphides are produced having an increased content of free sulphur.

The xanthic acid salt of formula (II) may be produced separately or in situ.

In a preferred embodiment of the process according to the present invention, the xanthic acid ester salt of the general formula (II) is produced in pure form in a separate process step according to known specifications; in this respect, see, for example, "Houben-Weyl: Methoden der Organischen Chemie; volume 9, p. 812 (1955)".

If an in situ production method is to be used, then, in a particularly preferred embodiment of the process according to the invention, the xanthate is produced from a mixture of carbon disulphide and the relevant alcohol in from 0 to 20 mol %, preferably from 3 to 15 mol % excess, based on $CS_2$, by adding drop-wise preferably 50% by weight soda lye, and the xanthate is directly further reacted without intermediate isolation. In the in situ-synthesis of the xanthate, the material may optionally be diluted with water to avoid the formation of xanthogen crystals, but the mol ratio of carbon disulphide to water should be less than 1:20, and preferably less than 1:10, because otherwise hydrolysis may easily occur with the formation of sodium sulphide. The process should be carried out at a temperature of less than 40° C., preferably from 0° to 20° C., for the same reason. The xanthate formation is completed after a maximum time of 12 hours and the reaction may be easily followed iodometrically.

The dilute chlorine bleach liquor is added to the xanthate or to the concentrated aqueous solution thereof with very thorough intermixing, as quickly as permitted by the cooling of the reactor, and the pH is simultaneously kept in the desired range of adding an acid, such as, for example, sulphuric acid, hydrochloric acid, nitric acid, phosphoric acid or acetic acid. The synthesis is best followed analytically by the iodometrically-controlled decrease of the xanthogen content. Since xanthogen disulphides are attacked oxidatively by chlorine bleach liquor in a slow reaction, among other things with the formation of sulphur, the synthesis is interrupted prematurely when there is a low residual content of xanthate. The residual content should be from 0.1 to 5 mol %, preferably from 1 to 3 mol %, based on the initial amount.

If the consumption of chlorine bleach liquor is plotted graphically against the xanthate conversion, then a strict proportionality is found, approximately up to a 95% conversion. From then on, the chlorine bleach liquor consumption increases over-proportionally (see Example 4e and graph 2). The generally conventional end point determination of the oxidation reaction using potassium iodide/starch paper can therefore not be applied in this case, in particular in the case of large mixtures where intermixing problems still exist.

In order to achieve a sufficiently thorough mixing of the chlorine bleach liquor into the reaction mixture, the liquor must be finely distributed directly at the inlet point, in the case of large mixtures. Thus, for example, a method of spraying the chlorine liquor into the liquid phase or into the gas chamber of the oxidation vessel has proved to be successful. One process is particularly preferred, in which the contents of the vessel are re-pumped through an external circuit, the chlorine bleach liquor being delivered into the side flow by a conventional mixing nozzle (injection nozzle).

Since the chlorine bleach liquor may be produced in the alkaline reaction medium by disproportionating chlorine, it is also possible to carry out the synthesis according to the invention using chlorine instead of chlorine bleach liquor. In order to avoid overoxidation of the xanthogen disulphide, the reaction has to be carried out using a chlorine flow which is heavily diluted with air or nitrogen, and a volume ratio of chlorine:inert gas of from 1:20 to 1:100 in particular has proved successful in this case.

If higher concentrated chlorine bleach liquor is used, then a local over-oxidation may occur. Where there is a particularly slow feed and a particularly thorough blending, the charge of such chlorine bleach liquors is possible in principle, but at the cost of a longer reaction time and a greater process unreliability. It is possible to carry out the oxidation process discontinuously in a reactor provided with a stirring apparatus, or continuously, for example, in a reactor cascade, a tubular or coil reactor or a screw apparatus.

The discontinuous method has proved to be advantageous with respect to the end point adjustment, whereas, in the continuous process, improved blending and simpler temperature control may be achieved. Therefore, the decision as to which type of process should be used merely depends on the respective operational factors.

The present invention also relates to the use of the xanthogen disulphides according to the invention as molecular weight regulators in the polymerisation of chloroprene for the production of benzene-soluble polymers. The xanthogen disulphides are suitable in particular for the production of light-coloured polychloroprene rubbers which have very good vulcanisation properties, the use thereof as raw materials for adhesives for the production of polychloroprene latices and also in admixture with cross-linked chloroprene polymers of the sol-gel type according to German Offenlegungsschrift No. 1,720,107.

The production of polychloroprene has been known for a long time and is described, for example, in Ullmanns Encyclopädie der technischen Chemie, Stuttgart, volume 9, P. 336 ff., Verlag Urban and Schwarzenberg, München-Berlin 1957 and in Encyclopädia of Polymer Science and Technology, Vol. 3, pages 705–730, John Wiley, New York 1965.

The process takes place in two stages, the polymerisation into latex being carried out in the first stage and the processing of the latex into solid rubber, for example by freezing coagulation, taking place in the second stage. The polychloroprene which is produced thus and vulcanized does not have the desired high strength level. This may be achieved when, instead of using mercaptan as the chain transfer agent, xanthogen disulphides, for example the xanthogen disulphide bis-(5-ethyl-1,3-dioxan-5-yl-methyl)xanthogen disulphide (MTX) is used. The xanthogen disulphide used as the chain transfer agent and produced according to this method provides a polymer which, after processing in a drier, exhibits a more or less heavy brown shade. This is attributed to the noticeable thermal or jet strain on the polymer during the drying process.

However, polymers which have a light brown inherent colour cannot be used, for example, for the production of mixtures for white sidewall car tyres or for the production of adhesives for light, transparent, discolouration-free bondings.

When added to polychloroprene latices, the xanthogen disulphides according to the invention have a clearly improved regulator efficiency and therefore they produce latices which have an improved stability in storage. Moreover, smaller quantities of activator are required.

As is known, 2-chlorobutadiene (chloroprene) is polymerised in an alkaline aqueous emulsion in the presence of radical initiators. It is also possible to polymerise chloroprene using different comonomers. Conventional comonomers are the following, for example: 1-chlorobutadiene, 2,3-dichlorobutadiene, styrene, isoprene, or acrylonitrile. The molecular weight of the resulting polymer is regulated by adding MTX, a chain-transfer agent. The polymerisation temperatures which may be from 5° to 80° C., are generally from 10° to 50° C. At these reaction temperatures, the polymerisation process is stopped when there is a monomer conversion of from 50 to 85%, usually from 60 to 70%. The following are used as suitable emulsifier systems: alkali metal salts of water-soluble, saturated or unsaturated monocarboxylic acids, for example, disproportionated resinic acids, optionally in admixture with fatty acids, such as oleic acid and coconut oil acids. The emulsifiers are added in quantities of from 2 to 10 parts by weight (preferably from 3 to 5 parts by weight), based on 100 parts of monomer.

Condensation products from naphthalene sulphonic acid and formaldehyde are also used as additional emulsifiers.

If the above-described emulsifier system is used, a pH of the emulsion higher than 10 is required. The pH should preferably be from 12 to 13.5.

The polymerisation process is started and carried out by adding known polymerisation initiators. Compounds which produce radicals are included as initiators, for example: alkali metal persulphates, hydrogen peroxide and organic peroxides such as cumene hydroperoxide or benzoyl peroxide. It is also possible to initiate polymerisation by adding reducing agents, such as formamidine sulphinic acid. Inhibitors such as phenothiazine terminate the polymerisation process. The remaining unreated monomer may be removed by steam distillation. The pH of the alkaline latex is reduced to pH 5 to 7 by dilute acetic acid and the polymer is isolated from this emulsion, for example by freezing coagulation, and it is dried, as described, for example, in Chem. Engng, Progr. 43, 391 (1974) and in German Pat. No. 1,051,506. However, other conventional methods are also suitable for processing, as described, for example, in German Pat. No. 1,111,804.

For the production of adhesives, the polychloroprene is dissolved in organic solvents such as benzene, toluene, methylene chloride or trichloroethylene or in mixtures of these solvents with other solvents which do not dissolve polychloroprene on their own, such as petrol, cyclohexane or methyl acetate.

The viscosity of the solution depends on the purpose of use and it is preferably from 10 to 100 poise, measured at 20° C. using a Brookfield-LVT-viscosimeter.

Other methods for the production of polychloroprene adhesives are described in German Auslegeschrift No. 1,200,988.

The following Examples illustrate the invention.

EXAMPLE 1

(a) A standard mixture for a chloroprene polymerisation process to test the regulating effect of bis-(5-ethyl-1,3-dioxan-5-yl-methyl)-xanthogen disulphide (MTX).

The following are introduced into a reactor at 44° C. (all parts are parts by weight):

| | |
|---|---|
| 125 | parts of distilled water, |
| 3.5 | parts of the Na—salt of a disproportionated abietic acid, |
| 0.65 | parts of the Na—salt of a condensation product of naphthalene sulphonic acid and formaldehyde, |
| 0.65 | parts of sodium hydroxide, |
| 100 | parts of chloroprene, and |
| 0.7 | parts of MTX. |

To initiate polymerisation, from 30 to 92 parts of a 2.5% by weight solution of formamidine sulphinic acid are allowed to flow into the reactor over a period of 3.5 hours. The quantity of activator solution depends on the sulphur content of the MTX, see Table 1.

When the monomer conversion is 66%, the reaction is stopped by adding phenothiazine. The remaining monomer is removed from the mixture by steam distillation. After lowering the pH to 7, the polymer is precipitated with 0.5% magnesium sulphate solution and the aqueous phase is decanted off. The product is washed until free of salt and is dried under vacuum over night at 70° C.

(b) HPLC determination of the sulphur content of bis-(5-ethyl-1,3-dioxan-5-yl-methyl)-xanthogen disulphide (MTX).

| Device | Liquid-chromatograph Perkin-Elmer, Series 2, UV detector Perkin-Elmer LC 15 Recorder Column 250 × 4.6 mm |
|---|---|
| Stationary phase: | Li-chromosorb Si 60, 5 mm |
| Mobile phase: | 30 ml n-butanol 27 ml acetonitrile made up to one liter with n-hexane |
| Throughflow: | 1.5 ml/min. |
| Injected quantity: | 5 µl |
| Injected solution: | 10 mg of MTX sample in a 25 ml measuring flask are weighed on an analytical balance and filled up with the mobile phase. |
| Temperature: | 25° C. |
| Rentention time: | Sulphur 2.3 min. MTX 4.7 min. |

The method was calibrated by weighing in sulphur up to the purest MTX.

Samples produced by weighing in sulphur up to the purest MTX produced the following Mooney viscosities:

TABLE 1

| S-content of the MTX (% by weight) | 0 | 0.5 | 1 | 2 | 4 | 8 |
|---|---|---|---|---|---|---|
| ML-4' value 100° C. | 34 | 36 | 38 | 56 | 73 | 140 |
| Activator consumption during polymerisation (parts by weight, see Example 1a) | 38 | 43 | 46 | 60 | 78 | 92 |

A number of the most varied MTX samples from different synthesis experiments were used as regulators according to Example 1a and the Mooney viscosities of the resulting elastomers were determined. The result is illustrated graphically on No. 1. The straight line shown corresponds to the values of Table 1. Graph 1 clearly proves the connection between the Mooney viscosity and the sulphur content of the regulator MTX. The individual values are relatively widespread, because the measurement of the Mooney viscosity may have an error of ±3 to 5%, depending on the measuring range, and the determination of small quantities of sulphur according to the HPLC analysis may contain an error of up to approximately 20%. The ML-4' value 50 is always exceeded when the sulphur content in the MTX is greater than 1.7%.

In the case of MTX batches having high sulphur contents of more than 2%, overproportionally large Mooney viscosity measurements often result. This effect derives from other unknown impurities in the MTX, which are a result of oxidative damage. They are probably polysulphides as preliminary stages of sulphur deposition which are not recorded as sulphur in the HPLC analysis but which act like sulphur in the polymerisation process.

Table 1 also shows the consumption of activator. It may be seen how the increasing sulphur content in the MTX also inhibits the polymerisation process which is expressed in the continuously increasing activator consumption. Polymer physical characteristics, such as for example the storage stability in hot air, measurable by the increase of the Mooney value by up to 25%, also deteriorate in parallel.

EXAMPLE 2

Production of bis-(5-ethyl-1,3-dioxan-5-yl-methyl)-xanthogen sulphide under different reaction conditions.

(A) xanthate synthesis:

The following are introduced into a reactor:

16.33 kg (112 mols) of 5-ethyl-5-hydroxymethyl-1,3-dioxane, 5.8 l (322 mols) of water, and 7.6 kg (100 mols) of carbon disulphide.

8.9 kg (111 mols) of 50% by weight soda lye are allowed to run in over a period of from 5 to 7 hours at from 10° to 15° C. The mixture is then stirred for a further 3 hours at 10° C. The iodometrically determined content of xanthate is 98%.

($B_1$) Oxidation 7.6 kg (4.55 mols) of chlorine bleach liquor having a concentration of 0.6 mol/kg, density $d20=1.97$, are initially run into the xanthate solution in a 250 l VA vessel provided with an anchor mixer (n=120 min.$^{-1}$) at from 5° to 10° C. The pH is then adjusted to 9 to 10 by adding 20% by weight sulphuric acid or hydrochloric acid and more chlorine bleach liquor of the concentration specified is then run in at from 5° to 10° C., the pH being maintained between 9 to 10 by the parellel addition of acid. The inflow is stopped when the iodometrically determined residual xanthate content still amounts to from 1 to 3% by weight of the starting quantity, approximately 108 kg (65 mols) of chlorine bleach liquor having been consumed. The suspension is filtered, washed free of chloride and dried under vacuum.

| Yield: | from 82 to 86%, based on $CS_2$ |
|---|---|
| Insoluble portion in acetone: | <0.1% |
| Free sulphur according to HPLC: The product is almost white, coarse-crystalline and easily pourable. | <0.5%, M.p. = 51–53° C. |

($B_2$) If the same experiment is carried out, but the mixer speed is reduced to n=25 min.$^{-1}$ in the oxidation stage, then an oily product is obtained which agglomerates in the vessel into spherical structures of such size that they cannot be removed via the bottom valve. It is impossible to determine the yield. It was found that the intermixing operation was inadequate.

| Colour: | Dark yellow |
|---|---|
| Mp: | 42–47° C. |
| Free sulphur content: | 1.9% |

EXAMPLE 3

Example 2 is repeated, as described, with a quantity of mixture of 12.2 k mol, based on $CS_2$, in a reactor of 23 m³ capacity with a crossbeam stirrer and flow disturbers at a stirrer speed of 65 min.$^{-1}$ (maximum speed). A yellow, oily product is obtained which clogs the filter pores and may only be filtered with the greatest difficulty. The filter cake bonds during this process into a very hard composition.

| Mp: | 48–53° C. |
|---|---|
| Sulphur content: | 1.2% |

The experiment is repeated, but a partial flow of the product, flowing at from 20 to 25 m³/hour, is repumped through a supply valve on the lid of the vessel from the bottom valve. The re-pumped flow is used as a propelling jet of a mixing nozzle, into which the chlorine liquor is metered in the side flow. Under otherwise indentical reaction conditions, an almost colourless product of outstanding crystallinity and outstanding filterability is obtained.

| Mp: | 51–53° C. | |
|---|---|---|
| Sulphur content: | 0.1% | |
| Yield: | 2.175 kg | 80.7% |

EXAMPLE 4

Example 2 is repeated, but the parameters of the oxidation stage indicated in each case in Table 2 are changed. Only Examples 4a and 4d are according to the invention. These products are indeed as required qualitatively, but the yields are clearly lower, in comparison with Examples 2 and 3. The Examples 4b, 4c and 4e are not according to the invention are are used for clarification purposes.

TABLE 2

| Example No. | T | pH | Residual xanthate | Assessment |
|---|---|---|---|---|
| 4 a | 15–20° C. | 9–10 | 1–3 mol-% | Yield: 65% S: 0.8–1% |
| 4 b | 35° C. | 9–10 | 3 mol-% | Yield: 2% |
| 4 c | 5–10° C. | 6–7 | Experiment not completed, release of $CS_2$ | |
| 4 d | 5–10° C. | 11–12 | 2 mol-% | Yield: 63% |
| 4 e | 5–10° C. | 9–10 | overoxidised to approx. 5% | Oily product S: 1.9% |

Figure 2:
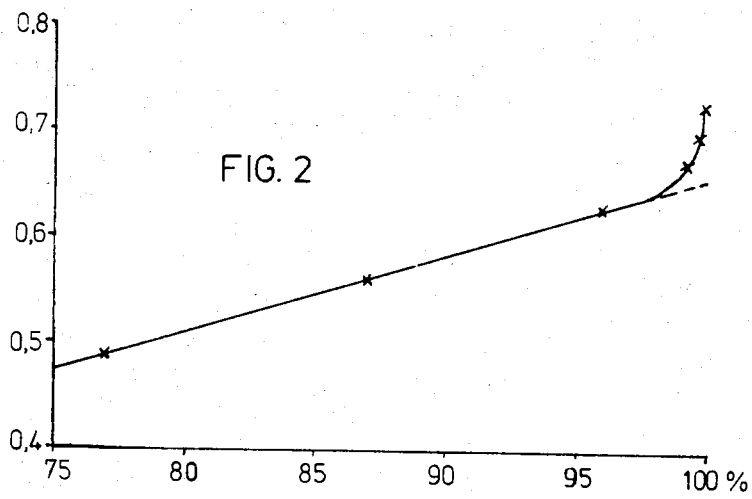

In Example 4e, the xanthate conversion was recorded as a function of the NaOCl consumption in the vicinity of the end point. Up to approximately 97% conversion, the relation is strictly linear; the remaining xanthate may then only be reacted further by using overproportional quantities of chlorine bleach liquor, see FIG. 2. It may be inferred from this that where there is a high conversion and primarily where there is overoxidation, secondary reactions come to the fore and they must be absolutely avoided to obtain a good quality product.

EXAMPLE 5

Diethyl xanthogen disulphide

The following are introduced into a round flask:
51.5 g (1.12 mol) of ethanol,
58 ml (3.22 mol) of water, and
76 g (1.0 mol) of carbon disulphide.

89 g (1.1 mol) of 50% by weight soda lye are added dropwise over a period of 6 hours at from 5° to 10° C. The mixture is stirred over-night and the orange-coloured solution is diluted with 60 ml of water. Approximately 100 ml of a chlorine bleach liquor having a concentration of 0.62 mol/l are added dropwise at from 5°–7° C. and the pH is then adjusted to 9 using 20% by weight sulphuric acid. Oxidation is carried out with more chlorine bleach liquor up to an iodometrically determined xanthogen conversion of 97%. The lower organic phase is separated and is degassed under vacuum at approximately 40° C.

| Yield: | 84 g | 76% based on $CS_2$. | The product crystallises upon standing |
|---|---|---|---|
| M.p: | 22–24° C. | | |
| Sulphur content: | 0.88% | | |

EXAMPLE 6

Bis-cyclohexyl xanthogen disulphide 112 g (1.12 mol) of cyclohexanol,
58 ml (3.22 mol) of water,
76 g (1.0 mol) of carbon disulphide, and
89 g (1.1 mol) of 50% by weight soda lye were reacted as in Example 5.

After oxidation with chlorine bleach liquor up to an iodometrically determined xanthogen conversion of 97%, a viscous yellow oil is obtained.

| Yield: | 110 g | 67% based on $CS_2$ |
|---|---|---|
| Sulphur content: | 0.58% | |

EXAMPLE 7

Continuous production of
bis-(5-ethyl-1,3-dioxan-5-yl-methyl)xanthogen disulphide (A) Xanthate synthesis:

The xanthate was produced according to Example 2A.

(B) Oxidation:

The following are continuously introduced into a 2-vessel cascade (filling volume 2.5 l/1.3 l):
773 g/h (2 mol/h) of xanthate solution,
743 ml/h (1.3 mol/h) of chlorine bleach liquor,
~450 ml/h of sulphuric acid (25% by weight), and
1.3 l/h of water.

The temperature was maintained at from 5° to 10° C. in the first vessel and it was from 10° to 15° C. in the second vessel. The pH values were 10 to 11 in both vessels. The residence time was 42 minutes in vessel 1 and 24 minutes in vessel 2. During a passage time of 9 hours, the xanthogen disulphide was obtained in a yield of from 75 to 79%.

| M.p. = | from 51 to 53° C. |
|---|---|
| Free sulphur according to HPLC = | 0.3% |

EXAMPLE 8 (Comparative Example)

The production of bis-(5-ethyl-1,3-dioxan-5-yl-methyl)-xanthogen disulphide (MTX) is carried out as described in German Offenlegungsschrift No. 2,306,610. A yellowish product is obtained having a melting point of from 45° to 51° C.

EXAMPLE 9 (Comparative Example)

The xanthogen disulphide obtained according to Example 8 is purified by recrystallization as follows.

The moist, not yet dried MTX is dissolved in acetone and the solution is filtered. An MTX acetone phase and an $H_2O$-salt phase are formed. By digesting twice with water and subsequent separation of the aqueous phase, the material is freed from water, salt and acetone. It is then remixed with isopropanol and acetone and is heated to approximately 30° C., so that all the MTX dissolves. It is then cooled to 0° C., and the MTX which has crystallized is suction-filtered and dried.

An almost white, fine-crystalline product, having a melting point of from 50° to 51° C. is obtained.

EXAMPLES 10 to 12

The MTX produced according to Examples 2A and $B_1$ as well as Examples 8 and 9 is used as a regulator in a chloroprene polymerisation process. Polymerisation is carried out as follows:

| | |
|---|---|
| (M) = Monomer phase: | |
| Chloroprene | 100.0 parts by weight |
| MTX according to Examples 8, 9, 2A + B$_1$ | 0.7 parts by weight |
| (W) = aqueous phase: | |
| Desalted water | 130.0 parts by weight |
| Sodium salt of a disproportionated abietic acid | 4.0 parts by weight |
| Sodium salt of a condensation product of naphthalene sulphonic acid and formaldehyde | 0.7 parts by weight |
| Caustic soda | 0.63 parts by weight |
| (A) = Activator phase: | |
| 2.5% by weight of aqueous formamidine sulphinic acid solution. | |

The aqueous and monomer phases are mixed in a 20 l reactor and the resulting emulsion is mixed with 5 parts of the activator phase. The reaction starts easily at an internal temperature of 40° C. The polymerisation heat which is generated is removed through external cooling and the polymerisation temperature is maintained at +45° C. When the monomer conversion is 66%, the reaction is stopped by adding phenothiazine. The remaining monomer is removed from the polymer by steam distillation and the polymer latex is frozen out on a cooling roller and is isolated after lowering the pH to 7.0. The Mooney viscosity and the activator consumption may be seen in the following Table.

| Example | MTX according to Example | Activator consumption (parts by weight) | ML'-4 (ME) |
|---|---|---|---|
| 10a | 8 | 62 | 58 |
| 11a | 9 | 50 | 47 |
| 12 | 2 A + B$_1$ | 38 | 35 | a Comparative Example

EXAMPLES 13 to 15

The polymer latices produced according to Examples 10 to 12 are frozen out on a cooling roller and are dried in a drier, as described in German Offenlegungsschrift No. 1,051,506. The rubber produced according to the invention then has a lighter inherent colour. In order to assess the colour, the polymers were dissolved in toluene (20% by weight). 1 mm thick films were cast from this solution and, after drying, sample cards (RAL) of the Committee for delivery terms and quality reliability at the German Standards Committee (DNA), 6 Frankfurt/M.1 Gutleutstr. 163-167, were allocated to the colours thereof.

| Example | Polymer according to Example | Polymer colour according to RAL |
|---|---|---|
| 13a | 10a | 1015 |
| 14a | 11a | 1013 |
| 15 | 12 | 9001 |

It clearly emerges from the Tables that a substantially improved regulator efficiency at a lower activator consumption is achieved with the regulator produced according the invention (Example 12) and a rubber having a light inherent colour may be produced (Example 15).

EXAMPLES 16 to 18

For the production of polychloroprene adhesives, a mixture of the following composition was polymerised under a nitrogen atmosphere:

| | |
|---|---|
| Chloroprene | 100.0 parts by weight |
| MTX according to Examples 9, 9 or 2A + B$_1$) | 0.48–0.61 parts by weight |
| desalted water | 140.0 parts by weight |
| sodium salt of a disproportionated abietic acid | 6.0 parts by weight |
| sodium salt of a naphthalene sulphonic acid/formaldehyde-condensation product | 0.7 parts by weight |
| soda lye (100%) | 0.6 parts by weight |
| potassium peroxodisulphate | 0.1 parts by weight |

Polymerisation takes place at +10° C. with a continuous supply of 2% by weight aqueous formamidine sulphinic acid. When the monomer conversion is 71%, the reaction is stopped by the addition of 0.1 parts by weight of phenothiazine. Processing is carried out as described in Examples 10 to 12.

EXAMPLE 19: (adhesive strength)

By adding polyisocyanate, the setting rate and the immediate strength of adhesion is improved. A two-component adhesive of this type is produced by preparing the polymer as a 17% by weight solution in ethyl acetate/petrol 65°–95° C./toluene in a weight ratio of 2:2:1 with stirring, and mixing with 5 parts of triphenylmethane-4,4',4''-triisocyanate. The adhesive strength is determined on an NR vulcanized rubber according to DIN 53 273.

| Example | MTX according to Example | MTX quantity parts by weight | ML-4 of the polymer (ME) | peeling resistance of adhesion after 10 h (N/mm) |
| --- | --- | --- | --- | --- |
| 16a | 8 | 0.61 | 102 | 4 |
| 17a | 9 | 0.55 | 98 | 5.2 |
| 18 | 2 A + B₁ | 0.48 | 100 | 6.5 | a Comparative Example

As may be seen, the adhesive strength is clearly improved by the adhesives raw material produced according to the invention (Example 18).

EXAMPLE 20 (Comparative Example)

The xanthogen disulphide of 3-methoxybutanol-1 is produced according to German Offenlegungsschrift No. 2,156,453 and chloroprene is polymerised in the presence of 0.65 parts by weight, as described in Examples 10 to 12. After processing, a solid rubber is obtained having a Mooney viscosity of ML-4′=54 ME.

EXAMPLE 21

The process is carried out as described in Example 20, but the xanthate is produced under reaction conditions according to the invention, as described in Examples 2A and B₁.

The rubber has a Mooney viscosity of Ml-4′=ME.

We claim:

1. An xanthogen disulphide containing less than 1.7% by weight of elemental sulphur and of the formula:

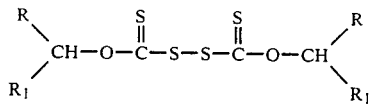

wherein each R is hydrogen, $C_1$–$C_6$-alkyl or $C_5$–$C_8$-cycloalkyl and each $R_1$ is 1,3-dioxolan-5-yl or said radical mono- to trisubstituted by $C_1$ to $C_4$ alkyl.

2. An xanthogen disulphide of claim 1 wherein each R is hydrogen and each $R_1$ is 5-ethyl-1,3-dioxan-5-yl.

* * * * *